(12) United States Patent
Kido

(10) Patent No.: US 10,524,751 B2
(45) Date of Patent: Jan. 7, 2020

(54) RADIOGRAPHIC IMAGING APPARATUS

(71) Applicant: Konica Minolta, Inc., Chiyoda-ku, Tokyo (JP)

(72) Inventor: Kazuhiro Kido, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 130 days.

(21) Appl. No.: 15/585,471

(22) Filed: May 3, 2017

(65) Prior Publication Data

US 2017/0325765 A1 Nov. 16, 2017

(30) Foreign Application Priority Data

May 16, 2016 (JP) ................................ 2016-097541

(51) Int. Cl.
*A61B 6/00* (2006.01)
*A61B 6/06* (2006.01)
*A61K 49/04* (2006.01)
*G06T 11/00* (2006.01)

(52) U.S. Cl.
CPC ................ *A61B 6/481* (2013.01); *A61B 6/06* (2013.01); *A61B 6/4035* (2013.01); *A61B 6/4258* (2013.01); *A61B 6/4291* (2013.01); *A61B 6/484* (2013.01); *A61B 6/5235* (2013.01); *A61K 49/0419* (2013.01); *G06T 11/003* (2013.01)

(58) Field of Classification Search
CPC ..... A61B 6/481; A61B 6/4035; A61B 6/4291; A61K 49/0419
See application file for complete search history.

(56) References Cited

U.S. PATENT DOCUMENTS

2014/0010344 A1* 1/2014 Nagatsuka ............... A61B 6/06
378/37

FOREIGN PATENT DOCUMENTS

JP 2006517558 A 7/2006

OTHER PUBLICATIONS

Velroyen A, Bech M, Malecki A, Tapfer A, Yaroshenko A, Ingrisch M, et al. Microbubbles as a scattering contrast agent for grating-based x-ray dark-field imaging. Physics in medicine and biology. Feb. 2013;58(4):N37-46. pmid:23369954 (Year: 2013).*

* cited by examiner

*Primary Examiner* — Eric D. Bertram
(74) *Attorney, Agent, or Firm* — Cantor Colburn LLP

(57) ABSTRACT

A radiographic imaging apparatus includes an imaging apparatus and a hardware processor. The imaging apparatus obtains moire fringe images for generating a reconstruction image of a subject by using a Talbot-Lau interferometer comprising a radiation source, a multiple slit, a first grating, a second grating and a radiation detector. The hardware processor performs a control to satisfy relations (i) $\varphi \geq (1/2) \times (R_s/R_1) \times d_1 > \varphi \times 0.7$, (ii) $1 \leq \varphi \leq 10$ (µm), and (iii) $0.5 \leq (R_s/R_1) \leq 1$. $\varphi$ is a particle size of a microbubble contrast agent to be used in imaging. $d_1$ is a slit period of the first grating. $R_1$ is a distance between the multiple slit and the first grating. $R_s$ is a distance between the multiple slit and the subject.

14 Claims, 10 Drawing Sheets

FIG. 9
(i)
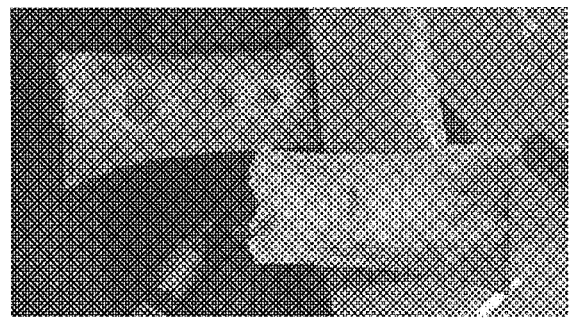
(ii)
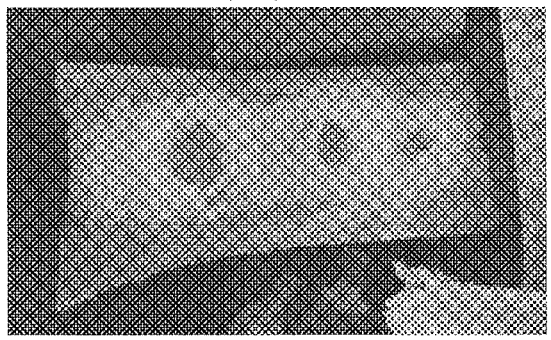
(iii)
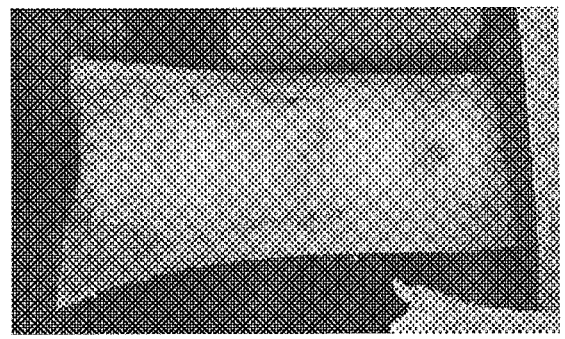
(iv)
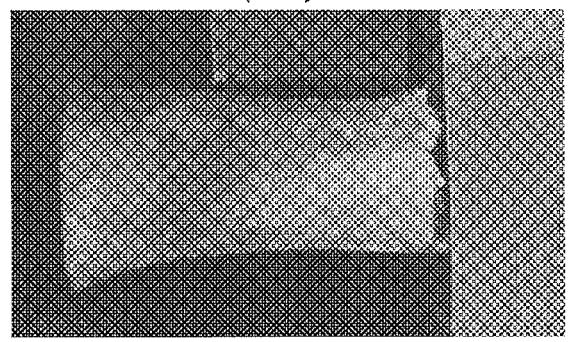

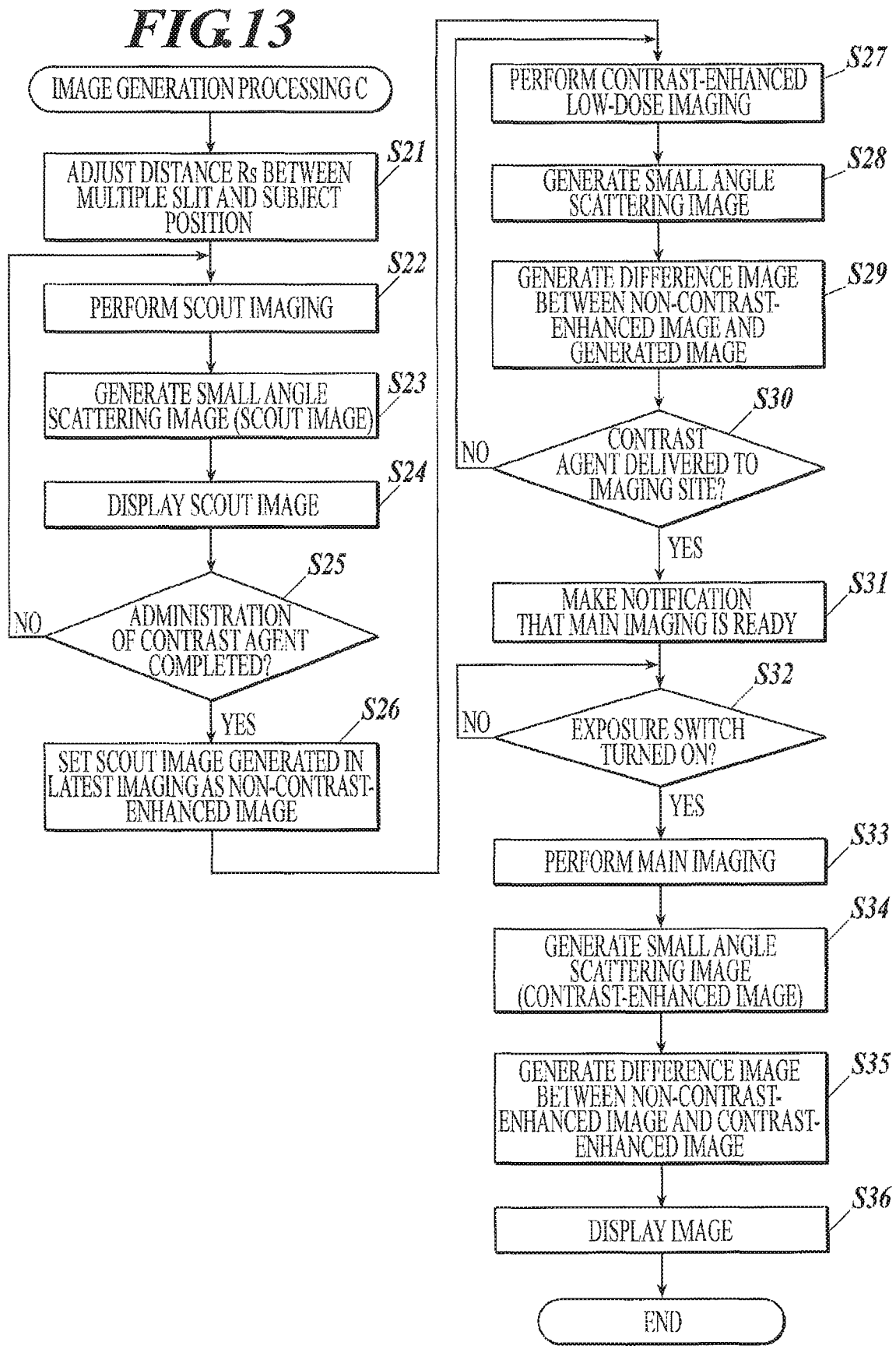

RADIOGRAPHIC IMAGING APPARATUS

CROSS REFERENCE TO RELATED APPLICATION

This application is based upon and claims the benefit of priority under 35 USC 119 of Japanese Patent Application No. 2016-097541 filed on May 16, 2016, the entire disclosure of which, including the description, claims, drawings and abstract, is incorporated herein by reference in its entirety.

BACKGROUND OF THE INVENTION

Technical Field

The present invention relates to a radiographic imaging apparatus.

Background Art

For ultrasonic diagnostic apparatuses, a diagnostic technique of cancer has been known in the art which involves imaging with a microbubble contrast agent and observing the resultant image. The use of a microbubble contrast agent enables, for example, visualizing new blood vessels. However, a problem with ultrasonic diagnostic apparatuses is that when a bone is present, a deeper site cannot be imaged. Further, another problem is that it is impossible to examine the whole body by a single administration of a contrast agent since the operator applies a probe to individual target sites to perform an examination.

On the other hand, Patent Document 1 (JP 2006-517558A) describes generating an image in which a microbubble contrast agent is depicted at high contrast by the DEI method, one of phase contrast techniques.

When a microbubble contrast agent is used for imaging a living body by means of a radiographic imaging apparatus using a Talbot-Lau interferometer, the microbubble contrast agent is visualized in a small angle scattering image which illustrates scattering by a microstructure. However, the signal of microbubbles is very weak in a small angle scattering image. Further, a small angle scattering image includes the signals of living body tissues as well as the signal of a microbubble contrast agent, which overlap with each other. Therefore, it is difficult to make a diagnosis.

SUMMARY OF THE INVENTION

It is an object of the present invention to improve the performance of visualizing a microbubble contrast agent in a reconstruction image that are generated from moire fringe images obtained by means of a radiographic imaging apparatus using a Talbot-Lau interferometer.

In order to realize the above object, according to one aspect of the present invention, there is provided a radiographic imaging apparatus, including:

an imaging apparatus which obtains moire fringe images for generating a reconstruction image of a subject by using a Talbot-Lau interferometer comprising a radiation source, a multiple slit, a first grating, a second grating and a radiation detector; and a hardware processor which performs a control so that $\varphi$, $d_1$ and $R_s/R_1$ satisfy following relations, where $\varphi$ is a particle size of a microbubble contrast agent to be used in imaging, $d_1$ is a slit period of the first grating, $R_1$ is a distance between the multiple slit and the first grating, and $R_s$ is a distance between the multiple slit and the subject.

$\varphi \geq (1/2) \times (R_s/R_1) \times d_1 > \varphi \times 0.7$ $1 \leq \varphi \leq 10$ (μm)

$0.5 \leq (R_s/R_1) \leq 1$

BRIEF DESCRIPTION OF THE DRAWINGS

The present invention will become more fully understood from the detailed description given hereinbelow and the appended drawings which are given by way of illustration only, and thus are not intended as a definition of the limits of the present invention, and wherein:

FIG. 9 illustrates a procedure of preparing a phantom of a bone tumor;

FIG. 13 is a flowchart of an image generation processing C that is performed by the hardware processor in FIG. 3.

DETAILED DESCRIPTION OF THE PREFERRED EMBODIMENT

Hereinafter, an embodiment of the present invention will be described with reference to the drawings. Though various technical limitations which are preferable to perform the present invention are included in the embodiment, the scope of the invention is not limited to the embodiment and the illustrated examples.

First Embodiment

Configuration of Radiographic Imaging Apparatus

Figure 1:
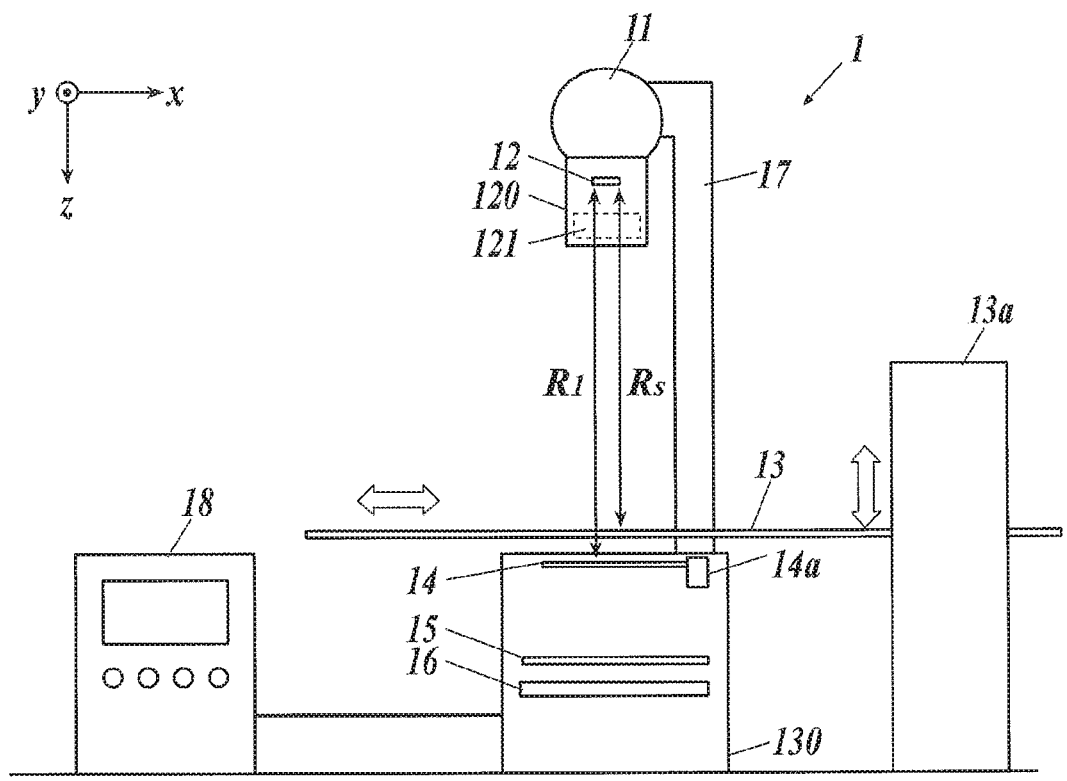
FIG. 1 illustrates an example of the configuration of a radiographic imaging apparatus.

FIG. 1 is a schematic view of a radiographic imaging apparatus 1 according to a first embodiment of the present invention.

As illustrated in FIG. 1, the radiographic imaging apparatus 1 performs X-ray imaging by using a Talbot-Lau interferometer and generates a reconstruction image from moire fringe images obtained by the X-ray imaging. The following description illustrates an example of a radiographic imaging apparatus that uses X-ray for imaging. However, other types of radiation such as neutron ray and gamma ray may also be used.

As illustrated in FIG. 1, the radiographic imaging apparatus 1 includes an imaging apparatus and a main body 18. The imaging apparatus includes a first covered unit 120 including a radiation source 11 and a multiple slit 12, a second covered unit 130 including a subject table 13, a first grating 14, a second grating 15 and a radiation detector 16, and a pillar 17. The radiographic imaging apparatus 1 is of a vertical type, and the radiation source 11, the multiple slit 12, the subject table 13, the first grating 14, the second grating 15 and the radiation detector 16 are arranged in the gravity direction or the z direction in the written order. As used herein, $R_0$ is the distance (mm) between the focal point of the radiation source 11 and the multiple slit 12, $R_d$ is the distance (mm) between the multiple slit 12 and the radiation detector 16, $R_1$ is the distance (mm) between the multiple slit 12 and the first grating 14, and $R_2$ is the distance (mm) between the multiple slit 12 and the second grating 15.

The distance $R_0$ is preferably from 5 mm to 500 mm, more preferably from 5 mm to 300 mm.

The distance $R_d$ is preferably equal to or less than 3000 mm since the height of a typical imaging room in a radiology department is approximately 3 m or less. In particular, the distance $R_d$ is preferably from 400 mm to 5000 mm, more preferably from 500 mm to 2000 mm.

The distance ($R_0+R_1$) between the radiation source 11 and the first grating 14 is preferably from 300 mm to 5000 mm, more preferably from 400 mm to 1800 mm.

The distance ($R_0+R_2$) between the focal point of the radiation source 11 and the second grating 15 is preferably from 400 mm to 5000 mm, more preferably from 500 mm to 2000 mm.

These distances may be selected based on their optimal values at which the grating image (self image) of the first grating 14 overlap on the second grating 15, which are calculated from the wavelength of the radiation emitted from the radiation source 11.

The radiation source 11, which includes an X-ray tube, generates an X-ray by means of the X-ray tube to emit it in the z direction (gravity direction). The X-ray tube may be, for example, a Coolidge X-ray tube or a rotating anode X-ray tube, which are both generally used in the medical field. The anode may be made of tungsten, molybdenum or the like.

The focal point diameter of the radiation source 11 is preferably from 0.03 mm to 3 mm, more preferably from 0.1 mm to 1 mm.

The first covered unit 120 is provided integrally with the radiation source 11. As illustrated in FIG. 1, the first covered unit 120 includes the multiple slit 12, an irradiation field diaphragm 121 and the like. The components of the first covered unit 120 are covered with a covering member for protection.

Figure 2:
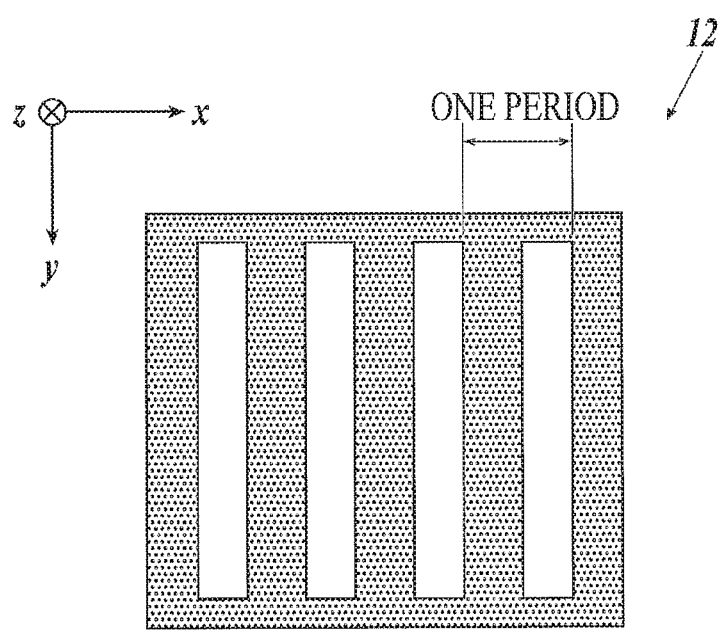
FIG. 2 is a plan view of a multiple slit.

The multiple slit 12 (G0 grating) is constituted by a diffraction grating. As illustrated in FIG. 2, slits are arranged at predetermined intervals in the x direction perpendicular to the irradiation axis of the radiation (z direction in the figure). The multiple slit 12 is made of a material having high shielding property against radiation, i.e. high absorption of radiation, such as tungsten, lead or gold, which is formed on a substrate of a material having low absorption of radiation such as silicon or glass. For example, the multiple slit 12 is produced as follows. A resist layer is masked in the shape of slits by photolithography and is irradiated with UV ray so that the slit pattern is transferred to the resist layer. A slit structure having the same shape with the pattern is formed by the exposure, and a metal is embedded in the slit structure by electroforming.

The slit period (grating period) do of the multiple slit 12 is from 1 μm to 60 μm. A slit period corresponds to the distance between adjacent slits as illustrated in FIG. 2. The width of the slits (the length of each slit in the direction of the slit period (x direction)) is from 1% to 60%, more preferably from 10% to 40% of the slit period. The height of the slits (the height in the z direction) is from 1 μm to 500 μm, preferably from 1 μm to 150 μm.

The irradiation field diaphragm 121 defines the irradiation field with the X-ray emitted from the radiation source 11.

The subject table 13 is provided to mount a subject thereon. To the subject table 13, a moving mechanism 13a for moving the subject table 13 in the x and z directions is attached. The moving mechanism 13a includes a first moving mechanism that ascends/descends the subject table 13 in the z direction by means of a driving motor or the like and a second moving mechanism that linearly forwards the subject table 13 in the x direction by means of a driving motor or the like.

As illustrated in FIG. 1, the second covered unit 130 includes the first grating 14, a forwarding mechanism 14a, the second grating 15, the radiation detector 16 and the like. The second covered unit 130 protects the components housed therein from a damage caused by a contact with a patient or a technician and a penetration of dust. Further, the second covered unit 130 can reduce the fluctuation of the grating position due to thermal expansion of the first grating 14 and the second grating 15 or the like, since the inner temperature of the unit is less affected by the outside air.

As with the multiple slit 12, the first grating 14 (G1 grating) is constituted by a diffraction grating in which slits are arranged in the x direction perpendicular to the irradiation axis of the radiation or the z direction. As with the multiple slit 12, the first grating 14 may be formed by photolithography using UV ray. Alternatively, it may also be formed by the so-called ICP method, in which fine lines are formed in a silicon substrate by deep etching so that the grating structure is made of only silicon. The slit period $d_1$ of the first grating 14 is from 1 μm to 20 μm. The width of the slits is from 20% to 70%, preferably from 35% to 60% of the slit period. The height of the slits is from 1 μm to 100 μm. Adjacent to the first grating 14, the forwarding mechanism 14a is provided to move the first grating 14 in the x direction. The forwarding mechanism 14a may have any configuration that can linearly forward the first grating 14 in the x direction by means of a driving motor or the like.

As with the multiple slit 12, the second grating 15 (G2 grating) is constituted by a diffraction grating in which slits are arranged in the x direction perpendicular to the irradiation axis of the radiation or the z direction. The second grating 15 may also be formed by photolithography. The slit period d2 of the second grating 15 is from 1 μm to 20 μm. The width of the slits is from 30% to 70%, preferably from 35% to 60% of the slit period. The height of the slits is from 1 μm to 100 μm.

In the embodiment, the grating planes of the first grating 14 and the second grating 15 are perpendicular to the z direction (i.e. parallel to the x-y plane), and the slit direction of the first grating 14 and the slit direction of the second grating 15 are mutually inclined from each other in the x-y plane by a predetermined (very small) degree, but they may also be disposed parallel to each other.

The radiation detector 16 includes a two-dimensionally arrayed conversion elements that generate electric signals according to received radiation. The radiation detector 16 reads the electric signals generated by the conversion elements as image signals. The pixel size of the radiation detector 16 is from 10 μm to 300 μm, more preferably from 50 μm to 200 μm. It is preferred that the radiation detector 16 is fixed such that it is in contact with the second grating 15. This is because the larger the distance between the second grating 15 and the radiation detector 16, the more the moire fringe image obtained by means of the radiation detector 16 is blurred.

The radiation detector 16 may be constituted by an FPD (flat panel detector). There are two types of FPDs, an indirect conversion type that coverts radiation to an electric signal by means of a photoelectric conversion element through a scintillator and a direct conversion type that directly coverts radiation to an electric signal, and any type of FPD may be used.

Further, the intensity modulating effect of the second grating 15 may be imparted to the radiation detector 16. For example, grooves may be formed in a scintillator in order to provide blind zones that have the same period and width of the second grating 15, and such a grating-shaped slit scintillator detector may be used as the radiation detector 16 (Reference 1: Simon Rutishauser et al., "Structured scintillator for hard X-ray grating interferometry", APPLIED PHYSICS LETTERS 98, 171107 (2011)). In this case, since the radiation detector 16 having such configuration can serve as both the second grating 15 and the radiation detector 16, it is not required to provide the second grating 15 separately.

Figure 3:
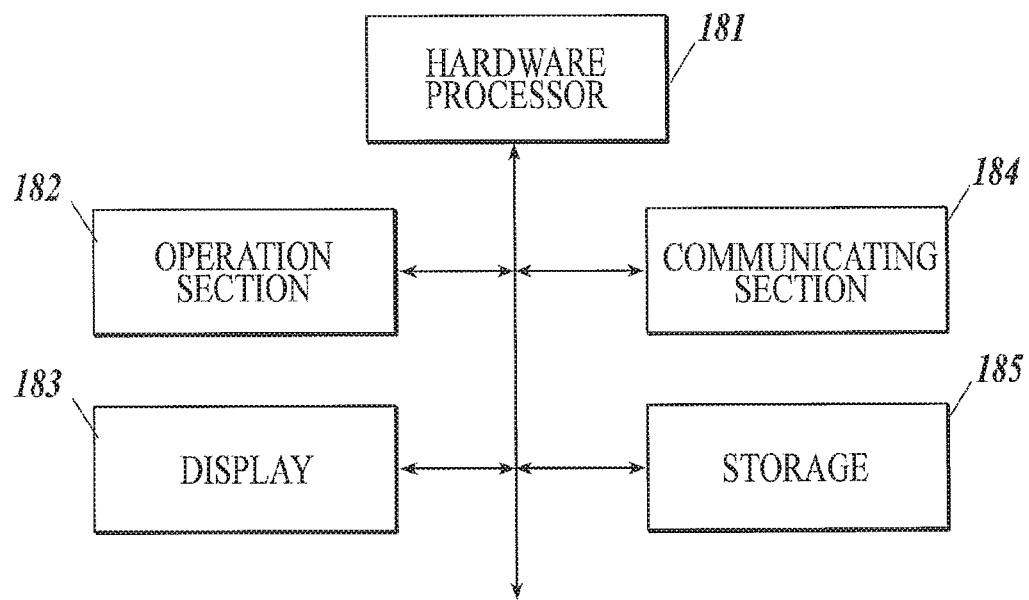
FIG. 3 is a block diagram of the functional configuration of a main body.

As illustrated in FIG. 3, the main body 18 includes a hardware processor 181, an operation section 182, a display 183, a communicating section 184 and a storage 185.

The hardware processor 181, which is constituted by a CPU (central processing unit), a RAM (random access memory) and the like, performs a variety of processing in cooperation with the programs stored in the storage 185. The hardware processor 181 is connected to the components outside the main body 18 (e.g. the radiation source 11, the radiation detector 16, the moving mechanism 13a, the forwarding mechanism 14a and the like). The hardware processor 181 controls these components of the radiographic imaging apparatus 1 to generate moire fringe images. Further, from the generated moire fringe images, the hardware processor 181 generates reconstruction images such as a small angle scattering image, an absorption image and a differential phase image, as well as a difference image which is described later.

The operation section 182 includes a touch panel integrally formed with the display 183 as well as an exposure switch and a set of keys for inputting the imaging conditions and the like. The operation section 182 generates an operation signal according to an operation and outputs it to the hardware processor 181.

The display 183 displays an operation screen, the operational status of the radiographic imaging apparatus 1, generated images and the like according to a display control of the hardware processor 181.

The communicating section 184, which includes a communication interface, communicates with an external apparatus such as a PACS (picture achieving and communication system, not shown in the figure) so as to send generated reconstruction images and a difference image to the external apparatus.

The storage 185 stores programs to be executed by the hardware processor 181 and data necessary for executing the programs. Further, the storage 185 stores moire fringe images obtained by means of the radiation detector 16.

While the radiographic imaging apparatus 1 is configured such that the radiation source 11 is disposed in the upper part to irradiate a subject thereunder with X-ray (so-called vertical type), it may also be configured such that the radiation source 11 is disposed in the lower part to irradiate a subject thereabove with X-ray. Further, the radiographic imaging apparatus 1 may also be configured such that X-ray is emitted in an arbitrary direction such as the horizontal direction (so-called horizontal type).

Operation of Radiographic Imaging Apparatus 1

An imaging method using the Talbot-Lau interferometer of the above-described radiographic imaging apparatus 1 will be described.

Figure 4:
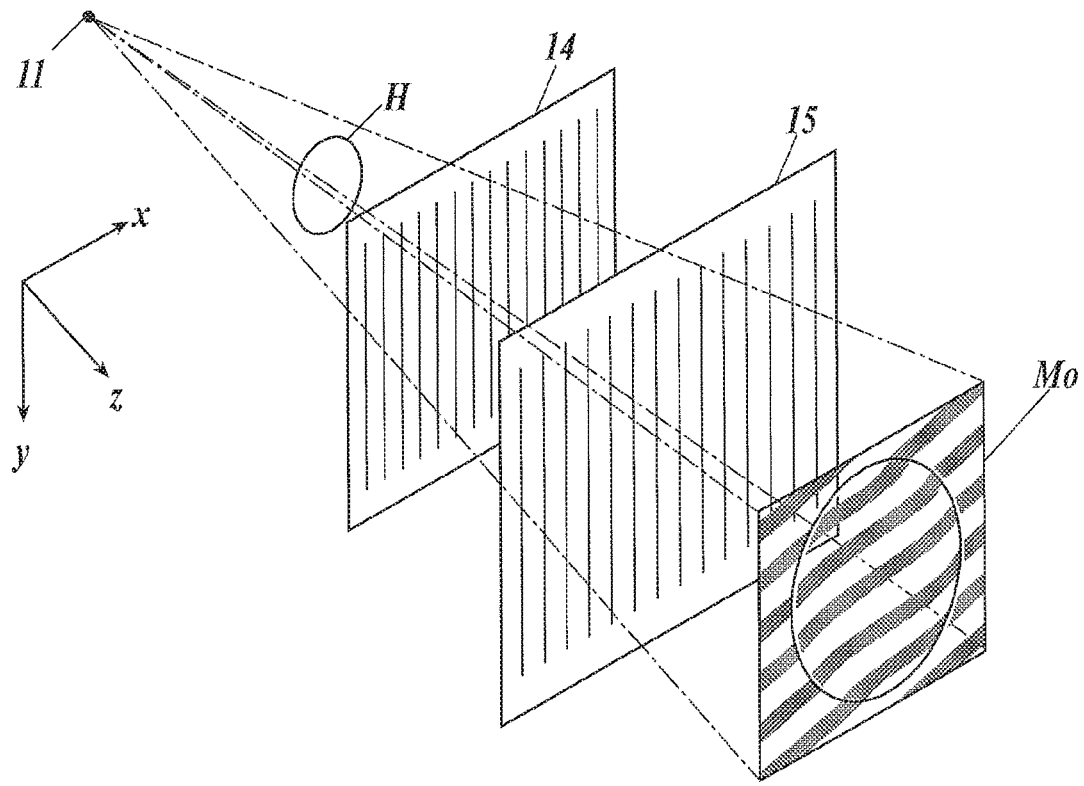
FIG. 4 illustrates the principle of a Talbot interferometer.

As illustrated in FIG. 4, when the X-ray emitted from the radiation source 11 passes through the first grating 14, the transmitted X-ray forms images at certain intervals in the z direction. The images are referred to as self images, and the phenomenon of forming self images is referred to as the Talbot effect. The second grating 15 is disposed at the position of a self image approximately parallel to the self image, and the X-ray that has passes through the second grating 15 forms a moire fringe image (designated as Mo in FIG. 4). That is, the first grating 14 forms a periodic pattern, and the second grating 15 transforms the periodic pattern into moire fringes. When a subject (designated as H in FIG. 4) is present between the radiation source 11 and the first grating 14, it shifts the phase of the X-ray so that the moire fringes in the moire fringe image discord along the outer edge of the subject as illustrated in FIG. 4. The discordance of the moire fringes can be detected by processing the moire fringe image, and the subject image can thus be visualized. This is the principle of a Talbot interferometer.

In the radiographic imaging apparatus 1, the multiple slit 12 is disposed between the radiation source 11 and the first grating 14 at a location closer to the radiation source 11 in order to achieve X-ray imaging by means of a Talbot-Lau interferometer. A Talbot interferometer basically requires that the radiation source 11 is an ideal point radiation source. However, a focal point with a relatively large diameter is used in actual imaging, which produces an effect as if the X-ray is emitted from an array of point radiation sources due to the multiple slit 12. This is the principle of X-ray imaging using a Talbot-Lau interferometer, which can produce the same Talbot effect as that of a Talbot interferometer even when the focal point diameter is relatively large.

In the radiographic imaging apparatus 1, moire fringe images that are required for generating a reconstruction image of a subject is captured by fringe scanning. Fringe scanning typically means to capture moire fringe image for M times (M steps of imaging) (M being a positive integer, and M>2 for an absorption image, and M>3 for a differential phase image and a small angle scattering image) while shifting one (the first grating 14 in the embodiment) or two of the gratings (the multiple slit 12, the first grating 14 and the second grating 15) relatively in the slit period direction (the x direction), so as to obtain M moire fringe images required for generating a reconstruction image. Specifically, when the slit period of the grating to be shifted is d μm, M moire fringe images are obtained by repeating a process of capturing an image and shifting the grating in the slit period direction by d/M μm. Then, based on the M moire fringe images, at least a small angle scattering image and an absorption image are generated, and a difference image between the generated small angle scattering image and the generated absorption image is further generated.

Hereinafter, an imaging operation and an image generating operation of the radiographic imaging apparatus 1 will be described.

Figure 5:
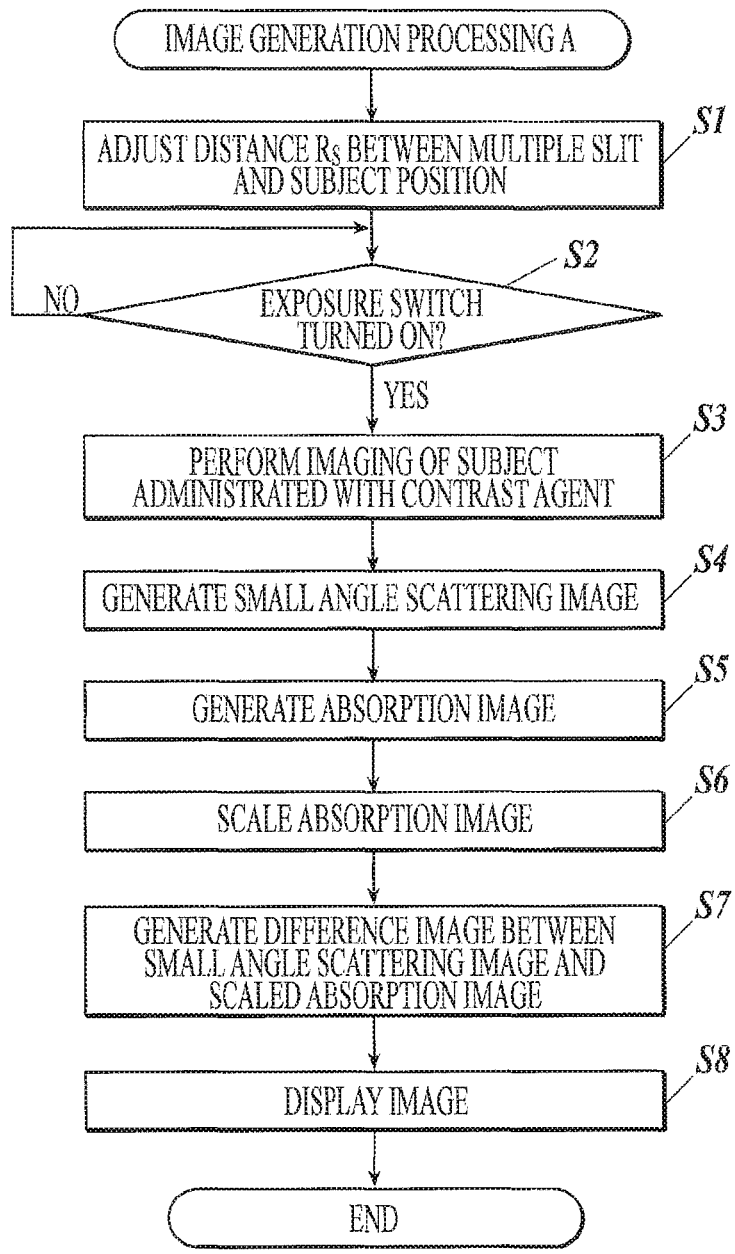
FIG. 5 is a flowchart of an image generation processing A that is performed by a hardware processor in FIG. 3.

FIG. 5 is a flowchart of an image generation processing A that is performed by the hardware processor 181 of the radiographic imaging apparatus 1. The image generation processing A is performed by the hardware processor 181 in cooperation with the programs stored in the storage 185. The image generation processing A involves imaging with a microbubble contrast agent and generating an image.

First, the hardware processor 181 controls the moving mechanism 13a to adjust the distance Rs between the multiple slit 12 and a subject position (Step S1).

In Step S1, Rs is adjusted so that the following relations (1) to (3) are satisfied, where φ is the particle size of the microbubble contrast agent to be used in the imaging, $d_1$ is the period of the first grating 14, $R_1$ is the distance between the multiple slit 12 and the first grating 14, and $R_s$ is the distance between the multiple slit 12 and the subject.

$$\varphi \geq (1/2) \times (R_s/R_1) \times d_1 > \varphi \times 0.7 \quad (1)$$

$$\varphi \leq \varphi \leq 10 \ (\mu m) \quad (2)$$

$$0.5 \leq (R_s/R_1) \leq 1 \quad (3)$$

In the embodiment, the subject position corresponds to the position of the subject table 13, and $R_s$ is the distance between the multiple slit 12 and the subject table 13.

The signal value V (x, y) of each pixel of a small angle scattering image is calculated by the following equation (4) from the X-ray intensity signal values $I_s$ (x, y) of the corresponding pixels of subject moire fringe images and the X-ray intensity signal values $I_r$ (x, y) of the corresponding pixels of BG moire fringe images. The subject moire fringe images refer to moire fringe images that are captured with the subject laid on the subject table 13. The BG (back ground) moire fringe images refer to moire fringe images that are captured without laying the subject on the subject table 13. $vis_s$ (x, y) is the definition of each pixel of the subject moire fringe images, and $vis_r$ (x, y) is the definition of each pixel of the BG moire fringe images. The larger the scattering, the lower the values of $vis_s$ (x, y), $vis_r$ (x, y) and V (x, y).

$$V(x, y) = \frac{vis_s(x, y)}{vis_r(x, y)} = \frac{\sum_{k=0}^{M-1} Ir_k(x, y) \left| \sum_{k=0}^{M-1} Is_k(x, y) \exp\left(-2\pi i \frac{k}{M}\right) \right|}{\sum_{k=0}^{M-1} Is_k(x, y) \left| \sum_{k=0}^{M-1} Ir_k(x, y) \exp\left(-2\pi i \frac{k}{M}\right) \right|} \quad (4)$$

Figure 6:
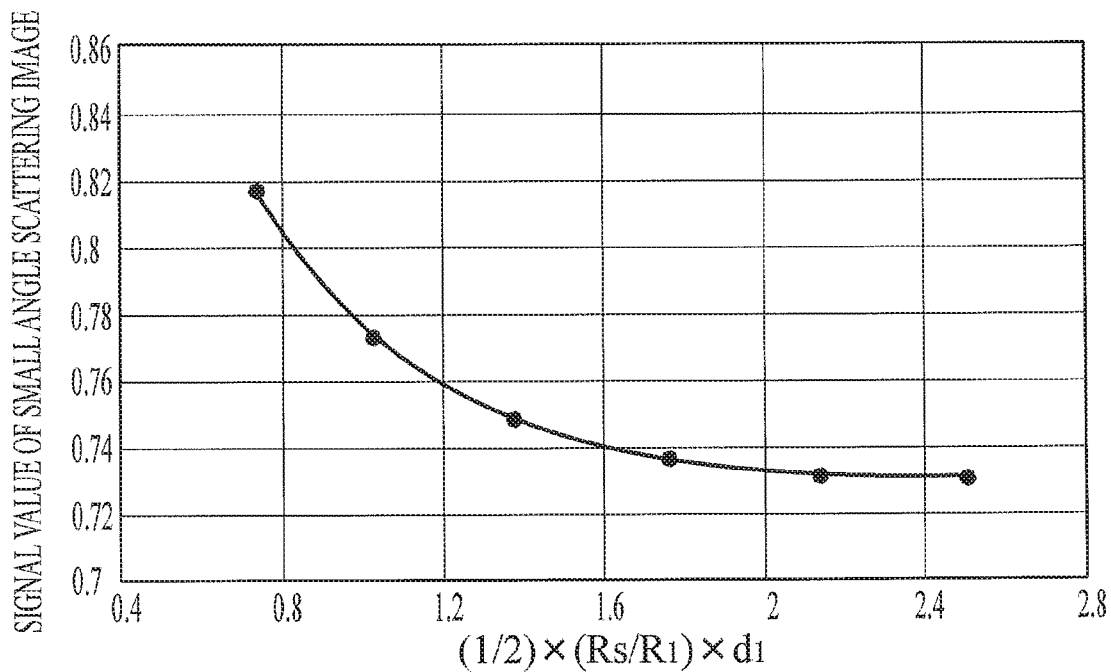
FIG. 6 is a graph in which signal values of the part of microbubbles in small angle scattering images are plotted, which are generated in different settings of $1/2 \times (R_s/R_1) \times d_1$.

FIG. 6 is a graph in which the signal values of the part of resin spheres as a substitute of microbubbles in the small angle scattering images are plotted, which are obtained at φ=2.5 μm and $d_1$=4.3 μm and different values of 1/2×($R_s$/$R_1$)×$d_1$ obtained by changing the value of $R_s$/R1. As illustrated in FIG. 6, when the value of 1/2×($R_s$/$R_1$)×$d_1$ is 2.5, i.e. when the value of 1/2×($R_s$/$R_1$)×$d_1$ is equal to the particle size φ of the microbubble contrast agent, the signal intensity of the microbubbles reaches the highest level (the detection sensitivity of the microbubbles becomes the highest). Further, when the value is φ×0.7=2.5×0.7=1.8 μm, the signal intensity of the microbubbles is sufficiently high (the detection sensitivity of the microbubbles is high). That is, the performance of visualizing a microbubble contrast agent can be improved by adjusting the value such that it satisfies the relation (1). Further, the lower the value of V (x, y), the higher the visualization performance.

The size of capillary vessels is typically equal to or less than 10 μm while the detectable limit of a Talbot-Lau interferometer is 1 μm. Accordingly, φ is preferably 1≤φ≤10 μm. Further, the resultant image is blurred when Rs/$R_1$ is low. Accordingly, Rs/$R_1$ is preferably 0.5≤$R_s$/$R_1$≤1.

For example, the microbubble contrast agent may be constituted by SONAZOID. The particle size φ of SONAZOID is from 2 μm to 3 μm. For example, when φ=2 μm and $d_1$=4 μm, $R_s$/$R_1$=1. That is, in Step S1, the hardware processor 181 controls the moving mechanism 13a to adjust $R_s$ so that $R_s$=$R_1$. Further, when φ=1 μm and $d_1$=4 μm, $R_s$/$R_1$=0.5. That is, in Step S1, the hardware processor 181 controls the moving mechanism 13a to adjust $R_s$ so that $R_s$=0.5$R_1$. In the adjustment, for example, the operator inputs the particle size of the microbubble contrast agent to be used on the operation section 182. In the embodiment, since $d_1$ and $R_1$ are fixed, the hardware processor 181 performs the adjustment by calculating the value of $R_s$ that satisfies the above-described relations (1) to (3).

It is preferred that the microbubble contrast agent is made of a shell material (e.g. a lipid or polymer) that is impregnated with glucose or coated with a coating agent containing glucose. Glucose is preferably used because it increases the detectability of cancer. Since cancer is incorporating glucose, such microbubble contrast agents are accumulated to new blood vessels of the cancer so that the signal contrast of the microbubbles is increased. Further, microbubble contrast agents do not require a facility for formulating a special radioactive drug such as one required in PET and are less invasive than contrast agents for PET.

Then, the hardware processor 181 waits until the operator turns on the exposure switch on the operation section 182 (Step S2).

In this step, the operator positions a subject on the subject table 13, injects (administers) the microbubble contrast agent to the subject and waits for a predetermined period of time until the contrast agent is delivered to the imaging target site. After the elapse of the predetermined period of time, the operator presses (turns on) the exposure switch on the operation section 182.

When the exposure switch is turned on (Step S2, Yes), the hardware processor 181 controls the radiation source 11, the radiation detector 16 and the forwarding mechanism 14a to perform plural steps (M steps) of imaging by fringe scanning so as to obtain a plurality (M sheets) of moire fringe images (Step S3).

In the imaging by fringe scanning, the emission of X-ray by means of the radiation source 11 is started when the first grating 14 is in a still condition. In the radiation detector 16, after a reset for removing residual unwanted electric charge due to the last imaging, electric charge is accumulated to coincide with the X-ray irradiation and then the accumulated electric charge is read out as an image signal to coincide with the shut-off of the X-ray irradiation. This corresponds to one step of imaging. To coincide with the end of each step of the imaging, the first grating 14 starts to be moved and then stopped at a predetermined distance. Then, the next step of the imaging is carried out. The travel distance of the first grating 14 is $d_1$/M. In this way, the move and pause of the first grating 14 is repeated corresponding to the predetermined steps while the irradiation with X-ray is performed and the image signal is read when the first grating 14 is in a still condition. The total travel distance of the first grating 14 reaches the length of one slit period when a series of imaging for obtaining a set of moire fringe images required for generating a reconstruction image is completed. After the imaging, the first grating 14 is returned to the original position.

Then, the hardware processor 181 generates a small angle scattering image from the set of moire fringe images (subject moire fringe image) obtained by the imaging (Step S4). The small angle scattering image can be generated by using the above-described equation (4). Previously-captured BG moire fringe images that are stored in the storage 185 are used. However, ones may be captured before or after capturing the set of subject moire fringe images.

Then, the hardware processor 181 generates an absorption image from the set of moire fringe images obtained by the imaging (Step S5). The signal value T (x, y) of each pixel of the absorption image is calculated from the X-ray intensity signal values $I_s$ (x, y) of the corresponding pixels of the subject moire fringe images and the X-ray intensity signal values $I_r$ (x, y) of the corresponding pixels of the BG moire fringe images by the following equation (5). In the equation, $a_{0s}$ (x, y) is the average intensity of the pixels of the subject moire fringe images, and $a_{0r}$ (x, y) is the average intensity of the pixels of the BG moire images.

$$T(x, y) = \frac{a_{0s}(x, y)}{a_{0r}(x, y)} = \frac{\sum_{k=0}^{M-1} Is_k(x, y)}{\sum_{k=0}^{M-1} Ir_k(x, y)} \quad (5)$$

Then, the hardware processor 181 performs scaling of the absorption image in order to adjust the signal level of a bone in the absorption image to the signal level of the bone in the small angle scattering image (Step S6).

Figure 7A:
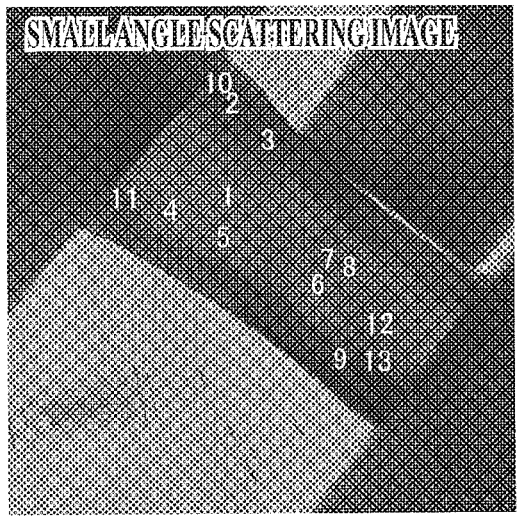
FIG. 7A is a small angle scattering image for generating an approximation function that is used for scaling an absorption image.
Figure 7B:
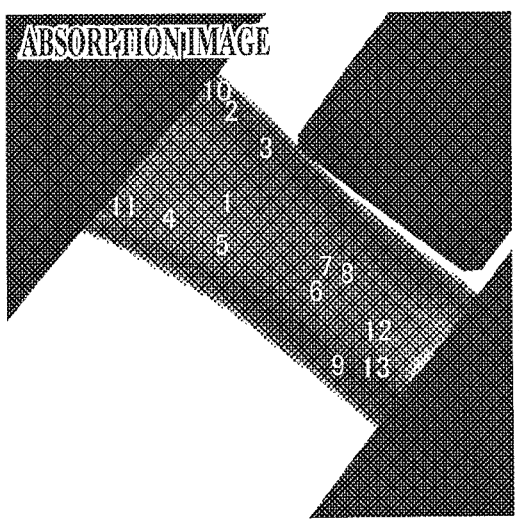
FIG. 7B is an absorption image for generating an approximation function that is used for scaling an absorption image.
Figure 8:
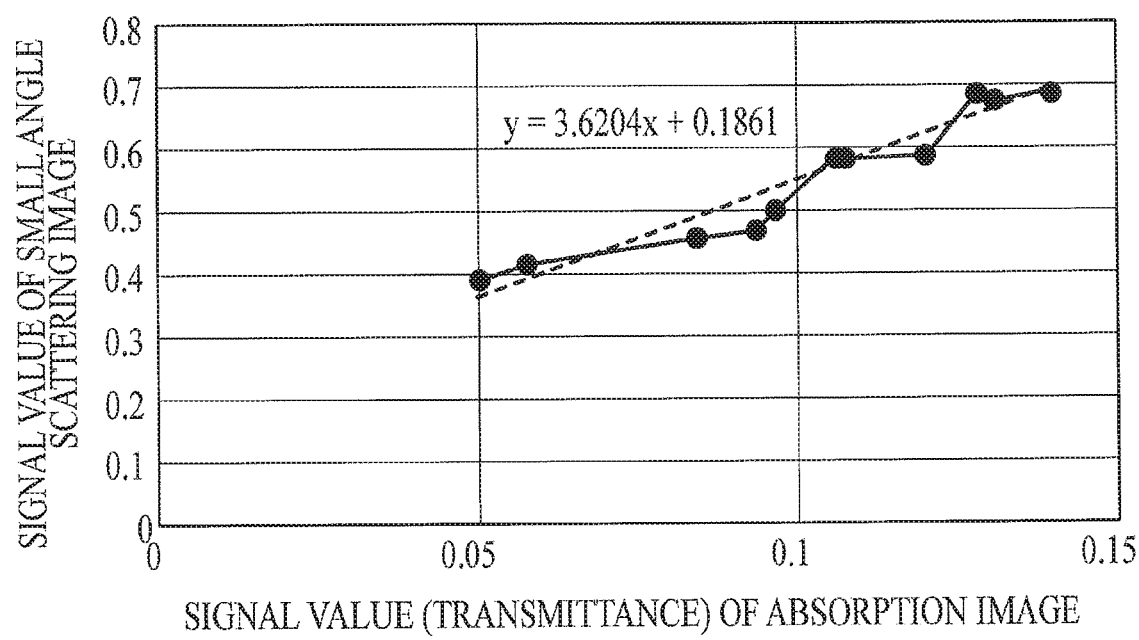
FIG. 8 is a graph for illustrating generation of an approximation function for scaling an absorption image.

As used herein, a small angle scattering image refers to an image that visualizes X-ray scattering in the subject, and an absorption image refers to an image that visualizes X-ray absorption of the subject. They are not completely identical but are similar in the part of a bone image as illustrated in FIG. 7A and FIG. 7B. Based on this, scaling is performed such that the signal values of a bone in the absorption image become similar to the signal values of the same part in the small angle scattering image. For example, the signal values of points (e.g. Point 1 to Point 13 in FIG. 7A and FIG. 7B) with different signal intensities are retrieved from a small angle scattering image that is generated from moire fringe images of the same site captured without administrating a contrast agent. Then, the signal values of the same points are retrieved from an absorption image that is generated from the same moire fringe images. The retrieved values are plotted on a graph in which the horizontal axis represents signal value of the absorption image and the vertical axis represents signal value of the small angle scattering image, and the approximation function thereof is determined as illustrated in FIG. 8. Then, the signal values of the absorption image generated in Step S5 are substituted in x of the determined approximation function, and the values of y are calculated. The signal values of the absorption image are thus converted to calculated values. It is preferred that the small angle scattering image and the absorption image before administrating the contrast agent, which are used for determining the approximation function, are generated from images that are captured after positioning the subject and before administrating the contrast agent. However, it may also be possible to use a small angle scattering image and an absorption image that are generated from images of the same site of a different person or images of a different tissue having a similar structure.

Then, the hardware processor 181 generates a difference image by subtracting the scaled absorption image from the small angle scattering image (Step S7). That is, the signal values of the pixels of the scaled absorption image are subtracted respectively from the signal values of the corresponding pixels of the small angle scattering image. The small angle scattering image and the scaled absorption image can be generated from the same moire fringe images. Accordingly, the subtraction can be performed at high accuracy without positional correction between the small angle scattering image and the absorption image.

Then, the hardware processor 181 displays the generated difference image on the display 183 (Step S8), and the image generation processing A ends.

Figure 10A:
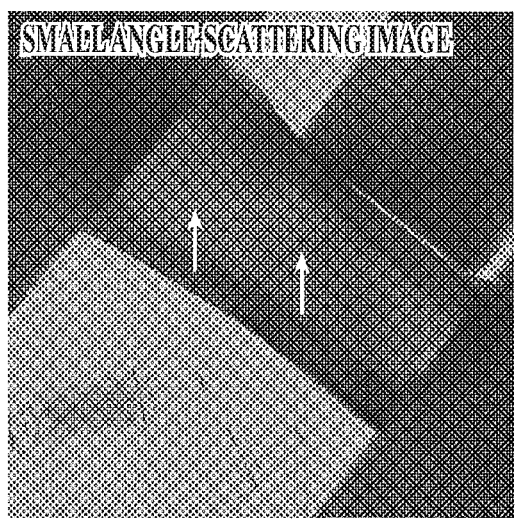
FIG. 10A is a contrast-enhanced small angle scattering image.
Figure 10B:
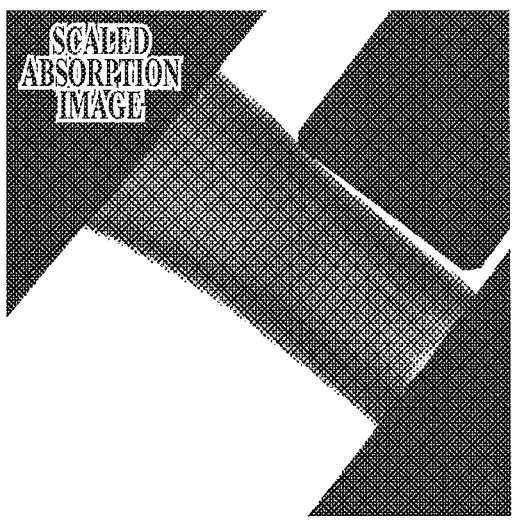
FIG. 10B is a scaled absorption image.
Figure 10C:
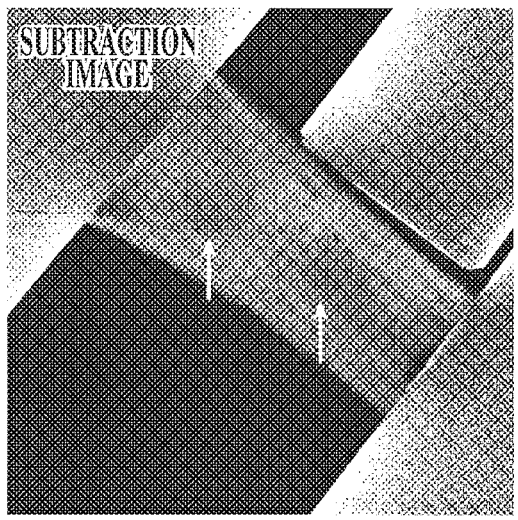
FIG. 10C is a reduction image (difference image) obtained by subtracting the image of FIG. 10B from the image of FIG. 10A.

FIG. 10A illustrates a small angle scattering image that is generated from moire fringe images of a bone tumor phantom prepared by the procedure illustrated in FIG. 9. FIG. 10B is the scaled absorption image of an absorption image generated from the same moire fringe images. FIG. 10C is a difference image that was obtained by subtracting the scaled absorption image of FIG. 10B from the small angle scattering image of FIG. 10A. A Talbot-Lau imaging apparatus having the following configuration and the following microbubble contrast agent were used for the imaging.

Grating period
Multiple slit: 22.8 μm
First grating: 4.3 μm
Second grating: 5.3 μm
Contrast agent: SONAZOID, particle size of 2-3 μm The bone tumor phantom was prepared by the following procedure.

First, a cattle bone was split and recesses were formed in one of the fractions as illustrated in FIG. 9 (i). Then, to simulate new blood vessels in a tumor, normal saline was injected into the recesses as illustrated in FIG. 9 (ii), and a microbubble contrast agent was further injected into the recesses as illustrated in FIG. 9 (iii). Then, the other bone fraction is placed thereon to cover it as illustrated in FIG. 9 (iv). The simulated new blood vessels of a tumor inside a bone in which a contrast agent is injected were thus prepared.

As illustrated in FIG. 10A, the signal of the contrast agent is depicted at high sensitivity but is poorly visible in the small angle scattering image since it overlaps with the signal of the bone. As illustrated in FIG. 10B, the contrast agent is not depicted in the absorption image. As illustrated in FIG. 10C, the area in which the microbubble contrast agent is injected is depicted at high visibility in the difference image that is obtained by subtracting the scaled absorption image of FIG. 10B from the small angle scattering image of FIG. 10A since the other signals than that of the microbubbles are reduced. That is, displaying such a difference image can improve the performance for making a diagnosis of inflammation or cancer (new blood vessels) where microbubbles are accumulated.

When displaying the difference image, the hardware processor 181 may add colors to the difference image according to the pixel values and overlay it on the absorption image. This enables observation of a lesion visualized by the microbubble contrast agent and observation of a tissue in a familiar absorption image for doctors to be made in the same image, which improves the ease of making a diagnosis.

As described above, the radiographic imaging apparatus 1 as illustrated in FIG. 1 is configured such that the moving mechanism 13a includes the second moving mechanism for forwarding the subject table 13 in the x direction (the direction of the body axis) so that the subject table 13 is movable in the direction of the body axis of the imaging subject according to a control of the hardware processor 181. Accordingly, in Step S3, the imaging may be performed at two or more sites while the subject table 13 is being moved. This enables performing whole body examination with a single administration of a contrast agent, which cannot be performed in an examination by means of an ultrasonic diagnostic apparatus.

Second Embodiment

Hereinafter, a second embodiment of the present invention will be described.

The second embodiment has the same configuration as the first embodiment. Accordingly, the description of the first embodiment applies to the second embodiment, and the operation of the second embodiment will be described below.

Figure 11:
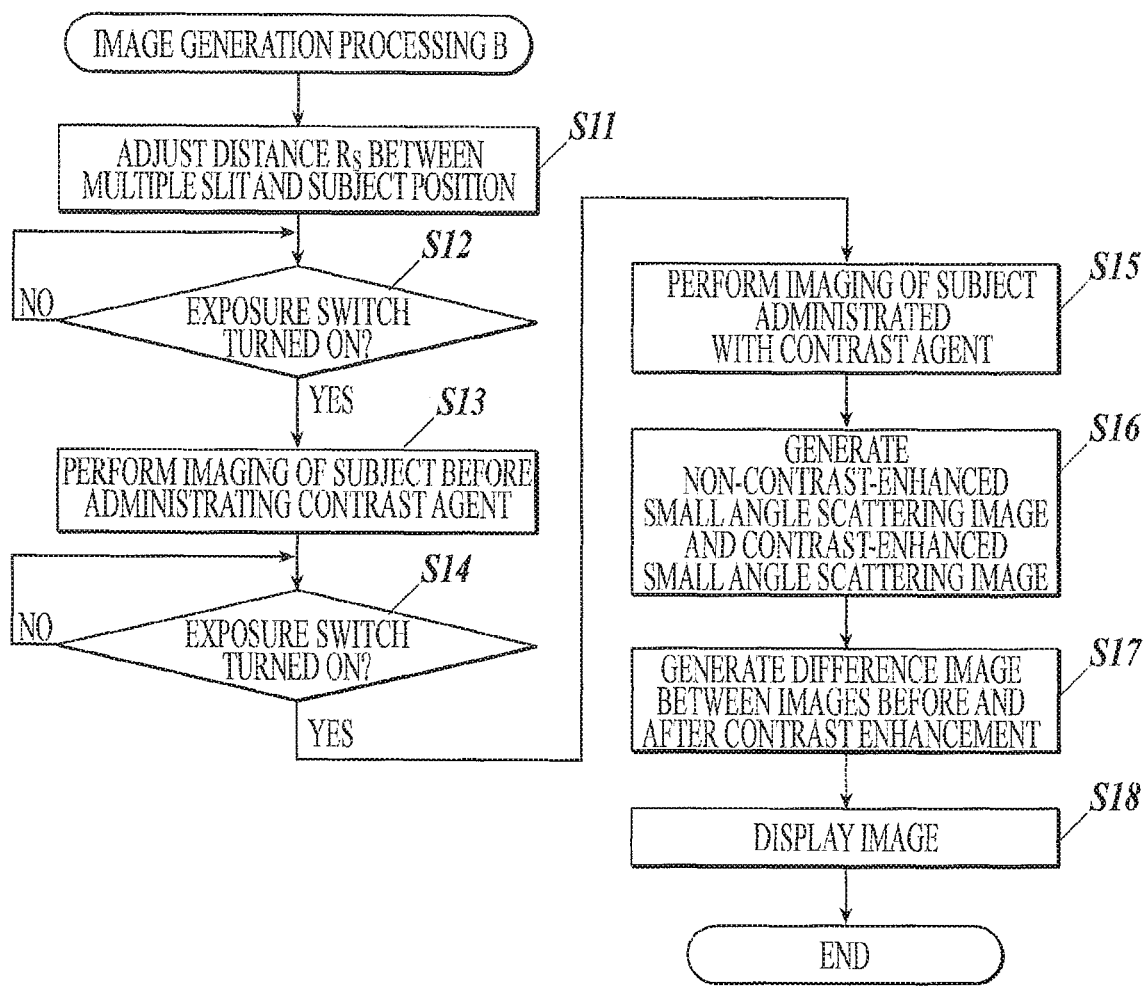
FIG. 11 is a flowchart of an image generation processing B that is performed by the hardware processor in FIG. 3.

FIG. 11 is a flowchart of image generation processing B that is performed by a hardware processor 181 of a radiographic imaging apparatus 1 according to the second embodiment. The image generation processing B is performed by the hardware processor 181 in cooperation with the programs stored in the storage 185.

First, the hardware processor 181 controls a moving mechanism 13a to adjust the distance $R_s$ between a multiple slit 12 and a subject position (Step S11). The processing in Step S11 is the same as that in Step S1, and the description of Step S1 applies to Step S11.

Then, the hardware processor 181 waits until the operator turns on an exposure switch on an operation section 182 (Step S12).

In this step, the operator positions a subject on the subject table 13.

When the exposure switch is turned on (Step S12, Yes), the hardware processor 181 controls the radiation source 11, the radiation detector 16 and the forwarding mechanism 14a to perform plural steps (M steps) of imaging by fringe scanning so as to obtain a plurality (M sheets) of subject moire fringe images before administration of a contrast agent (non-contrast-enhanced images) (Step S13).

After the imaging, the hardware processor 181 waits until the operator turns on the exposure switch on the operation section 182 (Step S14).

After the imaging before contrast enhancement, the operator injects a microbubble contrast agent to the subject and waits for a predetermined period of time until the contrast agent is delivered to the imaging target site. After the elapse of the predetermined period of time, the operator presses (turns on) the exposure switch on the operation section 182.

When the exposure switch is turned on (Step S14, Yes), the hardware processor 181 controls the radiation source 11, the radiation detector 16 and the forwarding mechanism 14a to perform plural steps (M steps) of imaging by fringe scanning so as to obtain a plurality (M sheets) of subject moire fringe images after administration of the contrast agent (contrast-enhanced images) (Step S15).

Then, the hardware processor 181 generates a non-contrast-enhanced small angle scattering image and a contrast-enhanced small angle scattering image from the respective pluralities of moire fringe images obtained by the imaging (Step S16). The small angle scattering images can be generated by using the above-described equation (4). Previously-captured BG moire fringe images that are stored in the storage 185 are used. However, ones may be captured before or after capturing the subject moire fringe images.

Then, the hardware processor 181 generates a difference image of the non-contrast-enhanced small angle scattering image and the contrast-enhanced small angle scattering image (Step S17). That is, the signal values of the pixels of the non-contrast-enhanced small angle scattering image are subtracted respectively from the signal values of the corresponding pixels of the contrast-enhanced small angle scattering image. It is preferred that one of the images is corrected by parallel shift, enlargement/reduction and the like so that they are aligned with each other before the subtraction.

Then, the hardware processor 181 displays the generated difference image on the display 183 (Step S18), and the image generation processing B ends.

In Step S18, the non-contrast-enhanced small angle scattering image and the difference image generated in Step S17 are displayed side by side (tiling display), or they are displayed in an alternately switchable manner according to an operation on the operation section 182.

Figure 12A:
FIG. 12A is a non-contrast-enhanced small angle scattering image.
Figure 12B:
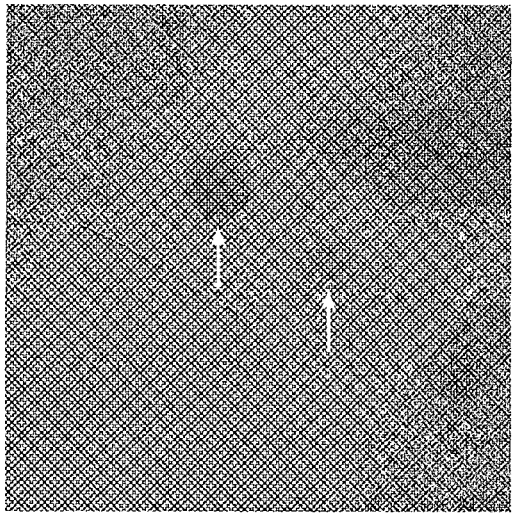
FIG. 12B is a difference image obtained by subtracting the small angle scattering image of FIG. 12A from the small angle scattering image of FIG. 10A.

FIG. 12B is a difference image that is generated by subtracting a non-contrast-enhanced small angle scattering image (see FIG. 12A) of a bone tumor phantom of FIG. 9B, which is prepared by placing the other bone without injecting the microbubble contrast agent, from a contrast-enhanced small angle scattering image (see FIG. 10A) of the bone tumor phantom prepared by the procedure as illustrated in FIG. 9A to FIG. 9D. In the difference image generated in the second embodiment, signals other than that of the microbubble contrast agent are reduced, and the parts where microbubbles are accumulated such as inflammations and cancers (new blood vessels) are depicted at high visibility as illustrated in FIG. 12B. That is, displaying such a difference image improves the performance for making a diagnosis of inflammation and cancer where microbubbles are accumulated. Further, in the non-contrast-enhanced small angle scattering image, the tissue of the imaging target site can be depicted at high visibility as illustrated in FIG. 12A. Therefore, displaying such a non-contrast-enhanced small angle scattering image and such a difference image side by side or in an alternately switchable manner enables both the tissue and a cancer or the like in the imaging target site to be readily observed, which can improve the ease of making a diagnosis. Further, the non-contrast-enhanced image and the difference image can be displayed at the same time or in an alternately switchable manner by a simple operation, which can reduce the burden on doctors.

To display the difference image, the hardware processor 181 may add colors to the difference image according to the pixel values and overlay it on the absorption image. This enables observation of a lesion visualized by the microbubble contrast agent and observation of a tissue in a familiar absorption image for doctors to be made in the same image, which improves the ease of making a diagnosis.

As described above, the radiographic imaging apparatus 1 as illustrated in FIG. 1 is configured such that the moving mechanism 13a includes the second moving mechanism for forwarding the subject table 13 in the x direction (the direction of the body axis) so that the subject table 13 is movable in the direction of the body axis of the imaging subject according to a control of the hardware processor 181. Accordingly, in Step S13 and Step S15, the imaging may be performed while the subject table 13 is moved. This enables performing whole body examination with a single administration of a contrast agent, which cannot be performed by means of an ultrasonic diagnostic apparatus.

Third Embodiment

Hereinafter, a third embodiment of the present invention will be described.

The third embodiment has the same configuration as the first embodiment. Accordingly, the description of the first embodiment applies to the third embodiment, and the operation of the third embodiment will be described below.

FIG. 13 is a flowchart of image generation processing C that is performed by a hardware processor 181 of a radiographic imaging apparatus 1 according to the third embodiment. The image generation processing C is performed by the hardware processor 181 in cooperation with the programs stored in the storage 185.

First, the hardware processor 181 controls the moving mechanism 13a to adjust the distance 1 between a multiple slit 12 and a subject position (Step S21). Step S21 is the same as Step S1, and the description of Step 1 applies to Step S21.

The operator lays and positions a subject on the subject table 13 and makes an order to start scout imaging on an operation section 182.

In response to a command for starting the scout imaging input on the operation section 182, the hardware processor 181 performs scout imaging (Step S22). The scout imaging refers to low-dose imaging that are performed at predetermined time intervals for checking the position. In Step S22, the hardware processor 181 performs plural steps (M steps) of low-dose imaging by fringe scanning so as to obtain a plurality (M sheets) of moire fringe images.

Then, the hardware processor 181 generates a small angle scattering image from the plurality of moire fringe images obtained in Step S22 (Step S23). The small angle scattering image can be generated by using the above-described equation (4). Previously-captured BG moire fringe images that are stored in the storage 185 are used. However, ones may be captured before or after capturing the subject moire fringe images. The small angle scattering image that is generated from moire fringe images obtained by the scout imaging is referred to as a scout image.

Then, the hardware processor 181 displays the generated scout image on the display 183 (Step S24). The operator checks the displayed scout image and makes a determination as to whether the position is correct, and adjusts the position if necessary. If the position is correct, the operator injects a microbubble contrast agent as described in the first embodiment to the subject and inputs completion of administrating the contrasting agent on the operation section 182.

Then, the hardware processor 181 makes a determination as to whether the completion of administrating the contrast agent is input on the operation section 182 (Step S25). If it is determined that the completion of administrating the contrast agent is not input (Step S25, No), the process returns to Step S22.

If it is determined that the completion of administrating the contrast agent is input (Step S25, Yes), the hardware processor 181 sets the scout image generated in the latest scout imaging as the non-contrast-enhanced image (non-contrast-enhanced small angle scattering image) (Step S26).

Then, the hardware processor 181 performs low-dose imaging after contrast enhancement (Step S27). The low-dose imaging after contrast enhancement refers to imaging that is performed with a low dose radiation at predetermined time intervals in order to detect whether the contrast agent has been delivered to the imaging target site. In Step S27, the hardware processor 181 performs plural steps (M steps) of low-dose imaging by fringe scanning so as to obtain a plurality (M sheets) of moire fringe images.

Then, the hardware processor 181 generates a small angle scattering image from the plurality of moire fringe images obtained in Step S27 (Step S28). The small angle scattering image can be generated by using the above-described equation (4).

Then, the hardware processor 181 generates a difference image of the non-contrast-enhanced image and the small angle scattering image generated in Step S28 (Step S29). That is, the signal values of the pixels of the non-contrast-enhanced image are subtracted respectively from the signal values of the corresponding pixels of the generated small angle scattering image. It is preferred that one of the images is corrected by parallel shift, enlargement/reduction and the like so that they are aligned with each other before the subtraction.

Then, the hardware processor 181 makes a determination as to whether the contrast agent has been delivered to the imaging target site based on the difference image generated in Step S29 (Step S30). For example, the hardware processor 181 determines that the contrast agent has been delivered to the imaging target site when the difference (absolute value) between the previous difference image and the current difference image is equal to or greater than a predetermined threshold.

If it is determined that the contrast agent has not been delivered to the imaging target site (Step S30, No), the process returns to Step S27.

If it is determined that the contrast agent has been delivered to the imaging target site (Step S30, Yes), the hardware processor 181 makes a notification that the main imaging is ready (Step S31). Specifically, it displays the notification that the main imaging is ready on the display 183. When the radiographic imaging apparatus 1 includes a voice output section, the notification that the main imaging is ready may be made by sound.

Then, the hardware processor 181 waits until the operator turns on the exposure switch on the operation section 182 (Step S32).

When the exposure switch is turned on (Step S32, Yes), the hardware processor 181 controls the radiation source 11, the radiation detector 16 and the forwarding mechanism 14a to perform the main imaging. That is, the hardware processor 181 performs plural steps (M steps) of imaging by fringe scanning so as to obtain a plurality (M sheets) of moire fringe images (Step S33).

Then, the hardware processor 181 generates a small angle scattering image from the plurality of moire fringe images obtained by the main imaging in Step S33 (Step S34). The small angle scattering image can be generated by using the above-described equation (4). The small angle scattering image generated from the moire fringe images obtained by the main imaging is referred to as a contrast-enhanced image (contrast-enhanced small angle scattering image).

Then, the hardware processor 181 generates a difference image by subtracting the non-contrast-enhanced image from the contrast-enhanced image (Step S35). That is, the signal values of the pixels of the non-contrast-enhanced image are subtracted respectively from the signal values of the corresponding pixels of the contrast-enhanced image. It is preferred that one of the images is corrected by parallel shift, enlargement/reduction and the like so that they are aligned with each other before the subtraction.

Then, the hardware processor 181 displays the non-contrast-enhanced image and the difference image on the display 183 (Step S36), and the image generation processing C ends.

The images displayed in Step S36 and the display manner thereof are the same as those in the second embodiment, and the third embodiment produces therefore the same advantageous effects as the second embodiment.

Further, the third embodiment is advantageous in that the delivery of the contrast agent to the imaging target site can be detected by means of low-dose radiation without capturing a motion picture.

When the hardware processor 181 detects that the contrast agent has been delivered to the imaging target site, it may calculate the radiation dose of the subsequent main imaging by subtracting the radiation dose of the last low-dose imaging in Step S27 from the preset specified radiation dose for the main imaging of the radiation source 11, and set the radiation dose of the radiation source 11 to the calculated radiation dose to perform the main imaging. Then, the hardware processor 181 may generate the contrast-enhanced small angle scattering image by adding the small angle scattering image generated from the moire fringe images obtained in the latest low-dose imaging to the small angle scattering image generated from the moire fringe images obtained in the main imaging, and then generates the difference image from the calculated contrast-enhanced small angle scattering image. This enables reducing the radiation dose of the main imaging and thus reducing the exposure of the subject.

As described above, in the radiographic imaging apparatus 1, the hardware processor 181 controls the components so that $\varphi$, $d_1$ and $R_s/R_1$ satisfy the relations (1) to (3), where $\varphi$ is the particle size of the microbubble contrast agent to be used in the imaging, $d_1$ is the slit period of the first grating 14, $R_1$ is the distance between the multiple slit 12 and the first grating 14, and $R_s$ is the distance between the multiple slit 12 and the subject.

This enables improving the performance of visualizing the microbubble contrast agent in a small angle scattering image.

The hardware processor 181 performs scaling so as to adjust the signal level of a bone in the absorption image generated from the captured moire fringe images to the signal level of the bone in the small angle scattering image generated from the same moire fringe images, and then generates the difference image by subtracting the scaled absorption image from the contrast-enhanced small angle scattering image. This enables obtaining a difference image in which signals other than that of the microbubble contrast agent are reduced so that the part where microbubbles are accumulated such as an inflammation or a cancer (new blood vessels) is depicted at high visibility, which can improve the performance for making a diagnosis of inflammation or cancer where the microbubbles are accumulated.

The hardware processor 181 generates the difference image between the non-contrast-enhanced small angle scattering image that is generated from the moire fringe image obtained before administrating the contrast agent to the subject, and the contrast-enhanced small angle scattering image that is generated from the moire fringe image obtained after administrating the contrast agent to the subject. This enables obtaining a difference image in which signals other than that of the microbubble contrast agent are reduced so that the part where the microbubbles is accumulated such as an inflammation or a cancer (new blood vessels) is depicted at high visibility, which can improve the performance for making a diagnosis of inflammation or cancer where microbubbles are accumulated.

The hardware processor 181 selects the small angle scattering image that is generated from the latest moire fringe images as the non-contrast-enhanced small angle scattering image from among the small angle scattering images that are generated from moire fringe images obtained by the imaging for checking the position (scout imaging) before administrating the contrast agent to the subject, and generates the difference image from the selected non-contrast-enhanced small angle scattering image. When scout imaging is performed, this eliminates the need for additionally imaging the subject before administrating the contrast agent, which can reduce the exposure of the subject.

The hardware processor 181 generates the difference images between the small angle scattering images that are generated from moire fringe images obtained by low-dose imaging at predetermined time intervals after administrating the contrast agent, and the non-contrast-enhanced small angle scattering image, and then detects the delivery of the contrast agent to the imaging target site based on the generated difference image. This enables detecting the delivery of the contrast agent to the imaging target site by means of low-dose radiation without capturing a motion picture.

When the hardware processor 181 detects the delivery of the contrast agent to the imaging target site, it displays a notification that the main imaging is ready on the display 183. This enables notifying the operator that the contrast-enhanced imaging is ready.

The hardware processor 181 generates the difference image from the contrast-enhanced small angle scattering image that is generated from moire fringe images captured after detecting the delivery of the contrast agent to the imaging target site. This enables generating the difference image reliably from the contrast-enhanced small angle scattering image.

The hardware processor 181 adds colors to the difference image according to the pixel values thereof and overlays it on the absorption image on the display 183. This enables observation of a lesion visualized by the microbubble contrast agent and observation of a tissue in the familiar absorption image for doctors to be performed in the same image, which improves the ease of making a diagnosis.

The hardware processor 181 displays the non-contrast-enhanced small angle scattering image and the generated difference image on the display 183 side by side or in an alternately switchable manner. This enables both the tissue and a cancer or the like in the imaging target site to be readily observed, which can improve the ease of making a diagnosis. Further, this can also reduce the burden on a doctor since the non-contrast-enhanced image and the difference image can be displayed together or in a switchable manner by a simple operation.

The above description of the embodiments merely illustrates suitable examples of the present invention, and the present invention is not limited thereto.

Figure 14:
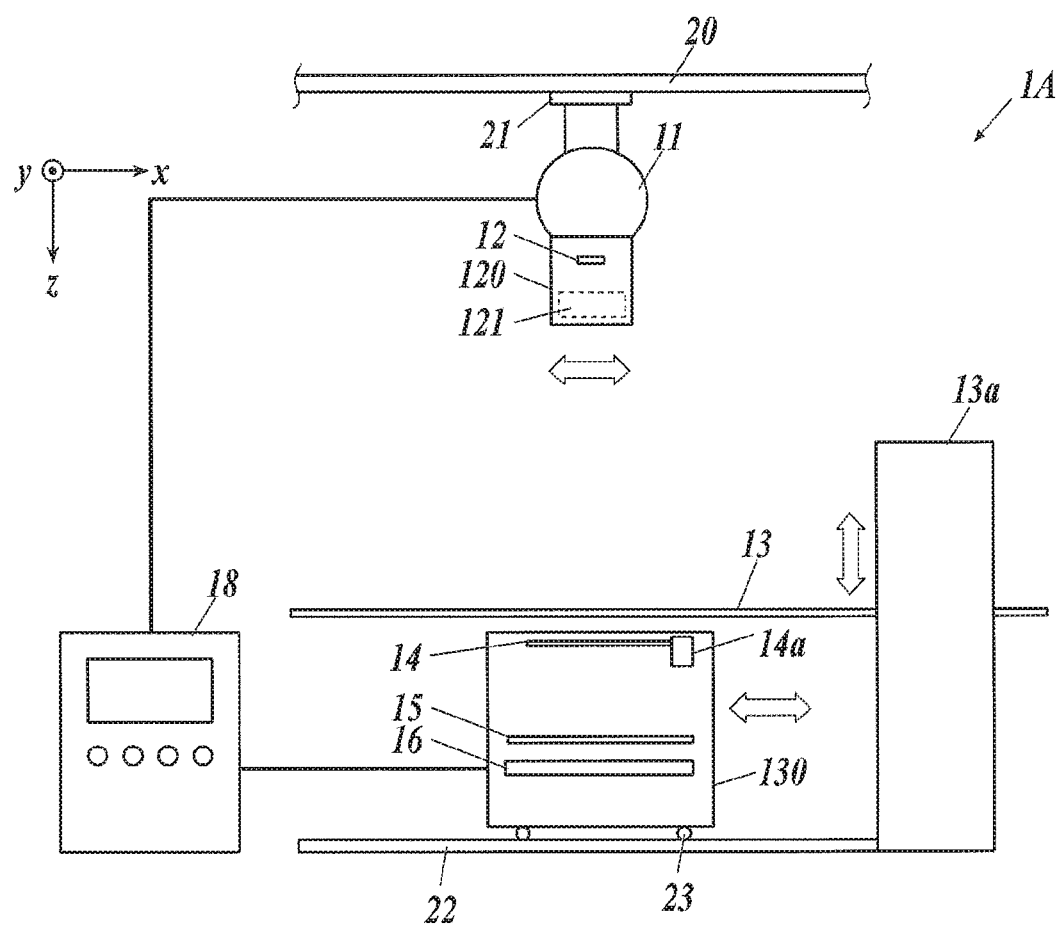
FIG. 14 illustrates another example of the configuration of the radiographic imaging apparatus.

For example, the above-described embodiment is an example in which the radiographic imaging apparatus is configured such that the subject table 13 is movable in the x direction relative to the first covered unit 120 including the radiation source 11 and the second covered unit 130 including the radiation detector 16. Instead, the first covered unit 120 including the radiation source 11 and the second covered unit 130 including the radiation detector 16 may be configured to be integrally movable in the x direction relative to the subject table 13 as in a radiographic imaging apparatus 1A in FIG. 14. For example, the radiographic imaging apparatus 1A may include a moving mechanism 21 that moves the first covered unit 120 linearly in the x direction along a rail 20 and a moving mechanism 23 that moves the second covered unit 130 linearly in the x direction along a rail 22, and the first covered unit 120 and the second covered unit 130 are integrally moved by the moving mechanisms 21, 23 under a control of the hardware processor 181.

The radiographic imaging apparatuses as described in the first to third embodiment may be applied to mammographic apparatuses that include a pressing plate for pressing a breast. Since images before and after contrast enhancement are captured while the breast is pressed by means of the pressing plate, the position of the subject is maintained at high accuracy between before and after the contrast enhancement. Therefore, little motion artifacts are produced, and it is possible to obtain a definite difference image including a low level of artifacts.

The radiographic imaging apparatus as described in the first to third embodiments may be used for imaging the joints of a patient with rheumatism before and after contrast enhancement. For example, the differential phase image that is generated from moire fringe images captured before contrast enhancement and a difference image between the small angle scattering images that are generated from moire fringe images captured before and after the contrast enhancement may be displayed side by side or in an alternately switchable manner on the display 183. The cartilage is depicted at high sensitivity in the differential phase image while inflammation (new blood vessels and blood flow) is depicted at high sensitivity in the difference image. This can improve the performance for detecting rheumatism.

The radiographic imaging apparatus may also be configured such that the first covered unit 120 and the second covered unit 130 rotates around the subject table 13 so that the subject is imaged from different directions. The moire fringe images thus obtained may be reconstructed into a 3D image so that a tomographic image at an arbitrary position can be displayed. This enables depicting a lesion without an interruption by an overlapped tissue.

The above-described embodiments are examples of the radiographic imaging apparatus using a Talbot-Lau interferometer in which the first grating 14 is moved relative to the multiple slit 12 and the second grating 15 during the imaging by fringe scanning. Instead, the present invention is also applicable to radiographic imaging apparatuses using a Talbot-Lau interferometer in which any one or two of the multiple slits 12, the first grating 14 and the second grating 15 are moved. Further, the present invention may also be applied to a Talbot-Lau interferometer using Fourier transformation, which does not require fringe scanning.

In addition, suitable changes can be made to the components, the detailed configuration and the detailed operation of the radiographic imaging apparatus without departing from the features of the present invention.

What is claimed is:

1. A radiographic imaging apparatus, comprising:
an imaging apparatus which obtains moire fringe images for generating a reconstruction image of a subject by using a Talbot-Lau interferometer comprising a radiation source, a multiple slit, a first grating, a second grating and a radiation detector; and
a hardware processor which performs a control so that $\varphi$, $d_1$ and $R_s/R_1$ satisfy following relations, where $\varphi$ is a particle size of a microbubble contrast agent to be used in imaging, $d_1$ is a slit period of the first grating, $R_1$ is a distance between the multiple slit and the first grating, and $R_s$ is a distance between the multiple slit and the subject:

$$\varphi \geq (1/2) \times (R_S/R_1) \times d_1 > \varphi \times 0.7;$$

$$1 \leq \varphi \leq 10 \ (\mu m);$$

$$0.5 \leq (R_s/R_1) \leq 1;$$

wherein the hardware processor generates a small angle scattering image from the moire fringe images obtained by the imaging apparatus; and
wherein the hardware processor generates a difference image between a non-contrast-enhanced small angle scattering image which is generated from moire fringe images obtained by the imaging apparatus before administrating the contrast agent to the subject and a contrast-enhanced small angle scattering image which is generated from moire fringe images obtained by the imaging apparatus after administrating the contrast agent to the subject.

2. The radiographic imaging apparatus according to claim 1, wherein $\varphi = (1/2) \times (R_s/R_1) \times d_1$.

3. The radiographic imaging apparatus according to claim 1, wherein the hardware processor generates an absorption image from the moire fringe images obtained by the imaging apparatus.

4. The radiographic imaging apparatus according to claim 3, wherein the hardware processor performs scaling on the absorption image so as to adjust a signal level of a bone in the absorption image to a signal level of the bone in the small angle scattering image, and generates a difference image by subtracting the scaled absorption image from the small angle scattering image.

5. The radiographic imaging apparatus according to claim 1, wherein the hardware processor selects a latest small angle scattering image generated from latest moire fringe images as the non-contrast-enhanced small angle scattering image from among small angle scattering images which are generated from moire fringe images captured by the imaging apparatus for checking a position before administrating the contrast agent to the subject, and generates the difference image from the non-contrast-enhanced small angle scattering image.

6. The radiographic imaging apparatus according to claim 1, wherein the hardware processor generates difference images between small angle scattering images that are generated from moire fringe images captured by the imaging apparatus at low-dose radiation at predetermined time intervals after administrating the contrast agent to the subject, and the non-contrast-enhanced small angle scattering image, and detects delivery of the contrast agent to an imaging target site based on the generated difference images.

7. The radiographic imaging apparatus according to claim 6, wherein the hardware processor makes a notification that main imaging is ready when detecting the delivery of the contrast agent to the imaging target site.

8. The radiographic imaging apparatus according to claim 6, wherein the hardware processor generates the difference image from the contrast-enhanced small angle scattering image which is generated from moire fringe images captured by the imaging apparatus after detecting the delivery of the contrast agent to the imaging target site.

9. The radiographic imaging apparatus according to claim 6,
wherein when detecting the delivery of the contrast agent to the imaging target site, the hardware processor calculates a radiation dose by subtracting a radiation dose of a latest low-dose imaging performed by the imaging apparatus from a preset specified radiation dose for main imaging of the imaging apparatus, sets the radiation dose of the imaging apparatus to the calculated radiation dose, and wherein the hardware processor generates the difference image from the contrast-enhanced small angle scattering image which is an image obtained by adding a first small angle scattering image to a second small angle scattering image, wherein the first small angle scattering image is generated from moire fringe images captured by the imaging apparatus in the last low-dose imaging, and wherein the second small angle scattering image is generated from moire fringe images captured by the imaging apparatus at the set radiation dose after detecting the delivery of the contrast agent to the imaging target site.

10. The radiographic imaging apparatus according to claim 1, wherein the hardware processor generates an absorption image from the moire fringe images obtained by the imaging apparatus, and adds a color to the generated difference image according to pixel values of the difference image, and overlays the colored difference image on the absorption image displayed on a display.

11. The radiographic imaging apparatus according to claim 1, wherein the hardware processor displays the non-contrast-enhanced small angle scattering image and the difference image on a display side by side or in an alternately switchable manner.

12. The radiographic imaging apparatus according to claim 1, further comprising:
a subject table; and
a moving mechanism which moves the subject table in a direction of a body axis of the subject.

13. The radiographic imaging apparatus according to claim 1, further comprising:
a subject table; and
a moving mechanism which integrally moves the radiation source and the radiation detector relative to the subject table.

14. The radiographic imaging apparatus according to claim 1, wherein the microbubble contrast agent is constituted by a contrast agent in which a shell material is impregnated with glucose or a contrast agent in which a shell material is coated with a coating agent containing glucose.

* * * * *